United States Patent [19]

Lamadrid et al.

[11] 4,256,442

[45] Mar. 17, 1981

[54] IMPROVED PRESSURE PLATE MOVEMENT SYSTEM FOR A PERISTALTIC PUMP

[75] Inventors: Rene G. Lamadrid, Bethesda; Herbert M. Cullis, Silver Spring, Md.

[73] Assignee: Baxter Travenol Laboratories, Inc., Deerfield, Ill.

[21] Appl. No.: 31,140

[22] Filed: Apr. 18, 1979

[51] Int. Cl.³ .................................... F04B 45/06
[52] U.S. Cl. ............................. 417/477; 417/475; 417/476
[58] Field of Search ............... 417/476, 475, 477; 251/9, 7, 4, 10; 74/491, 527; 222/207, 209, 214

[56] References Cited

U.S. PATENT DOCUMENTS

| | | | |
|---|---|---|---|
| 662,955 | 12/1900 | McClelland | 251/4 |
| 3,203,272 | 7/1965 | Fernberg | 74/527 |
| 3,227,091 | 1/1966 | Isreeli | 417/477 |
| 3,299,904 | 1/1967 | Burke | 251/9 |
| 3,447,478 | 6/1969 | Clemens | 103/149 |
| 3,582,234 | 6/1971 | Isreeli | 417/476 |
| 3,597,124 | 8/1971 | Adams | 417/477 |
| 3,675,653 | 7/1972 | Crowley | 128/278 |
| 3,731,555 | 5/1973 | Fresmann | 74/491 |
| 3,756,752 | 9/1973 | Stenner | 417/477 |
| 3,781,142 | 12/1973 | Zweig | 417/477 |
| 3,836,287 | 9/1974 | Grosholz et al. | 417/306 |
| 3,881,641 | 5/1975 | Pliml et al. | 417/476 |
| 3,927,955 | 12/1975 | Spirosa et al. | 417/477 |
| 3,963,023 | 6/1976 | Hankinson | 128/214 F |
| 3,990,444 | 11/1976 | Vlal | 128/214 F |
| 4,060,348 | 11/1977 | Della Bianca | 417/475 |
| 4,086,824 | 5/1978 | Johnson | 74/481 |
| 4,095,923 | 6/1978 | Cullis | 417/475 |

FOREIGN PATENT DOCUMENTS 1077932 3/1960 Fed. Rep. of Germany ............ 251/9

Primary Examiner—Carlton R. Croyle
Assistant Examiner—Rae Evans Cronmiller
Attorney, Agent, or Firm—Robert A. Benziger; Steven W. Weinrieb; Paul C. Flattery

[57] ABSTRACT

An improved peristaltic pump includes a pivotably mounted pressure plate which, together with the pump roller elements, defines the pump chamber. The pivotal mounting of the pressure plate facilitates accessibility to the pump chamber in order to simplify the pump tube loading and unloading procedures. The mounting system for the pressure plate includes a mechanically-advantaged four-bar linkage arrangement which automatically retains the pressure plate in either its fully open or fully closed position as a result of an over-center type locking construction. The pump also includes a mechanism for adjusting the volume flow rate characteristic of a pump tube. This is particularly adaptable for a dual-tube system wherein a predetermined volume flow rate ratio is to be achieved.

31 Claims, 5 Drawing Figures

IMPROVED PRESSURE PLATE MOVEMENT SYSTEM FOR A PERISTALTIC PUMP

FIELD OF THE INVENTION

The present invention relates generally to peristaltic pumps, and more particularly to improvements in peristaltic pumps utilized for pumping human blood fluids in conjunction with human blood cell separator apparatus, human blood dialysis apparatus, or the like.

BACKGROUND OF THE INVENTION

Peristaltic pumps, of the type wherein a plurality of roller elements move along the inner race of a cylindrical or semi-cylindrical stator casing in order to pump a fluid through a compressible plastic tube, having the requisite resiliency or memory, by means of intermittent compression and expansion reactions generated within the tube, are of course well known. One such conventional peristaltic pump is disclosed, for example, in U.S. Pat. No. 3,756,752 issued to Stenner. While the operability of the Stenner type pump has apparently proven to be quite satisfactory, the procedure required for operably inserting the compressible pump tube into the pumping chamber has proven to be difficult and tedious. This is due to the fact that the pumping chamber is essentially closed with the exception of a notch formed within a rotatable disk covering the pumping chamber. In order to insert the compressible pump tube within the pumping chamber, one end of the tube is initially disposed within the notch of the cover disk, and the disk is subsequently rotated so as to in effect feed or thread the tube about the rollers disposed within the pumping chamber.

Within blood cell separator systems, it has also proven necessary to sometimes employ pumping mechanisms which can simultaneously pump different fluids, at different volume flow rates, through separate tubes disposed within the pumping chamber. A conventional system of this type is exemplified by U.S. Pat. No. 3,060,348 issued to Della Bianca. As disclosed within such patent, the two compressible pump tubes are operatively associated with stepped pump roller elements. While the means for mounting or inserting the pump tubes within the pump chamber is not apparently disclosed in the Della Bianca patent, it has been attempted to utilize a multi-tube system, such as that shown in the Della Bianca patent, within a pumping system such as that disclosed within the Stenner patent. Such an adaptation, however, has proven extremely difficult to accomplish due to the fact that both tubes have to be simultaneously or separately fed into the pump chamber through the disk notch system of Stenner. In addition, it is also quite difficult and tedious to properly seat the pump tubes upon the roller elements as shown in the Della Bianca patent in order to assuredly accomplish the requisite pumping of both fluids. Still further, it is also necessary to be able to adjust the relative volume flow rates defined within the pump tubes such that, for example, the volume flow rate within one of the tubes has a value which is a predetermined ratio of the volume flow rate within the other tube. The aforenoted prior art does not provide such an adjustment means.

From the foregoing, it will be appreciated that in order to facilitate the mounting or insertion of the pump tubes within the pump chambers of peristaltic pumps, particularly in those instances wherein multi-tube systems are to be employed, it is virtually mandatory that the pump chambers be partially open or have means which render the same openable. In this manner, the requisite accessibility to the pump chambers is able to be established.

In U.S. Pat. No. 3,836,287 issued to Grosholz et al., there is disclosed peristaltic pump apparatus wherein the interior portion of the pump chamber is rendered accessible so as to facilitate the insertion or loading of the pump tube. This procedure is accomplished as a result of the provision of a pivotable cover or lid having integrally movable therewith an arcuate guide element which operatively cooperates with the pump rollers. The lid and guide element system, however, further comprises a relatively complex spring-biased plunger mechanism for properly positioning the roller guide element when the same is moved between its open and closed positions through means of a compound movement which includes both pivotable and translational modes. In addition, separate fastening or securing means must also be provided for securing the cover or lid of the pump mechanism to the pump base when the lid is in its closed position.

OBJECTS OF THE INVENTION

Accordingly, it is an object of the present invention to provide a new and improved peristaltic pump.

Another object of the present invention is to provide a new and improved peristaltic pump which overcomes the afore-noted disadvantages of the prior art.

Still another object of the present invention is to provide a new and improved peristaltic pump wherein the interior portion of the pump chamber is readily accessible so as to facilitate and simplify the pump tube loading and unloading procedure.

Yet another object of the present invention is to provide a new and improved peristaltic pump wherein the interior portion of the pump chamber is readily accessible so as to facilitate and simplify the pump tube loading and unloading procedures operatively conducted in connection with a multi-tube pumping system.

Yet still another object of the present invention is to provide a new and improved peristaltic pump which can readily accommodate a multi-tube pumping system wherein the relative volume flow rates defined within the tubes can be simply and accurately adjusted to predetermined ratio values.

Still yet another object of the present invention is to provide a new and improved peristaltic pump wherein the mounting system for the pump pressure plate or roller guide element is mechanically-advantaged and balanced such that auxiliary fastening means is not necessarily required in order to retain the pressure plate or guide element in either its open or closed position.

SUMMARY OF THE INVENTION

The foregoing and other objectives are achieved in accordance with the present invention through the provision of a peristaltic pump comprising a pump roller pressure plate which, together with the pump roller elements, serves to define the pumping chamber. The pressure plate is pivotably mounted upon the pump base so as to be movable between open and closed positions. In this manner, the interior portion of the pumping chamber is readily accessible when the pressure plate is moved to its open position so as to facilitate the insertion or loading of the pump tubes within the pumping chamber.

An operating handle is also pivotably mounted upon the pump base, and a pair of links pivotally interconnect the handle and the pressure plate. The pivot point locations or axes of the pressure plate, the interconnecting links, and the operating handle serve to define a four-bar linkage lever system. Furthermore, the pivotal axes of the components are so disposed relative to each other that the system exhibits characteristics somewhat similar to that of an over-center locking mechanism. As a result, when the handle is moved to either one of its extreme positions so as to in turn move the pressure plate to either its fully open or closed position, the lever system is properly balanced such that auxiliary fastening means need not be provided in order to retain the pressure plate in either its open or closed position. Detent means are in fact, however, defined between the operating handle and the links, as well as between the pressure plate housing and the pump base. Such detent means serve a two-fold purpose, the first of which is to additionally insure the fact that the pressure plate is retained in either its open or closed position, and the second purpose is to audibly indicate that the pressure plate has in fact attained either its open or closed position.

The peristaltic pump of the present invention is particularly well-suited to accommodate multi-tube pumping systems, and accordingly includes additional means for accurately adjusting the relative volume flow rates within the tubes. The adjustment means effectively elongates one of the pump tubes, preferably the small-diameter tube, by stretching the same, and as a result of this stretching action, the cross-sectional inner diameter of the tube is constricted. Consequently, the volume flow rate through the tube is altered. In order to accurately attain a predetermined flow rate through the tube, particularly relative to the flow rate existing within the other tube, ratio indicia is provided upon the flow rate adjustment means.

BRIEF DESCRIPTION OF THE DRAWINGS

Various other objects, features, and attendant advantages of the present invention will be more fully appreciated as the same becomes better understood from the following detailed description when considered in connection with the accompanying drawings, in which like reference characters designate like or corresponding parts throughout the several views, and wherein.

DETAILED DESCRIPTION OF THE PREFERRED EMBODIMENT

Figure 1:
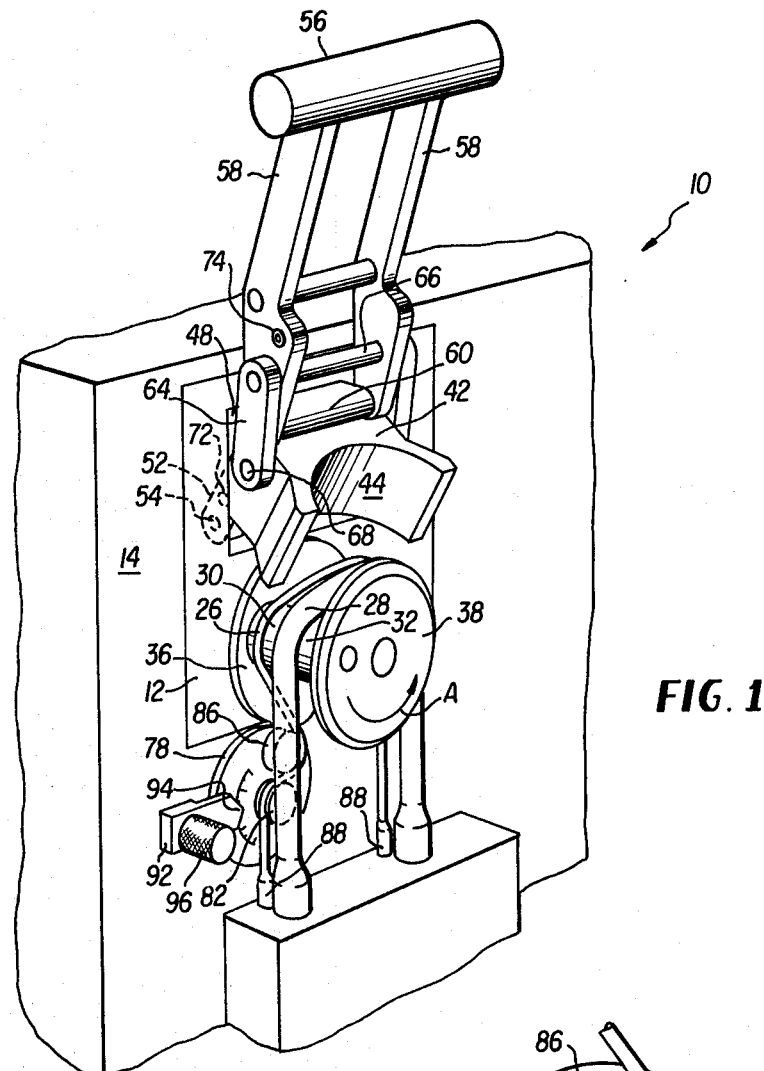
FIG. 1 is a perspective view of the peristaltic pump constructed in accordance with the present invention and showing its cooperative parts.
Figure 2:
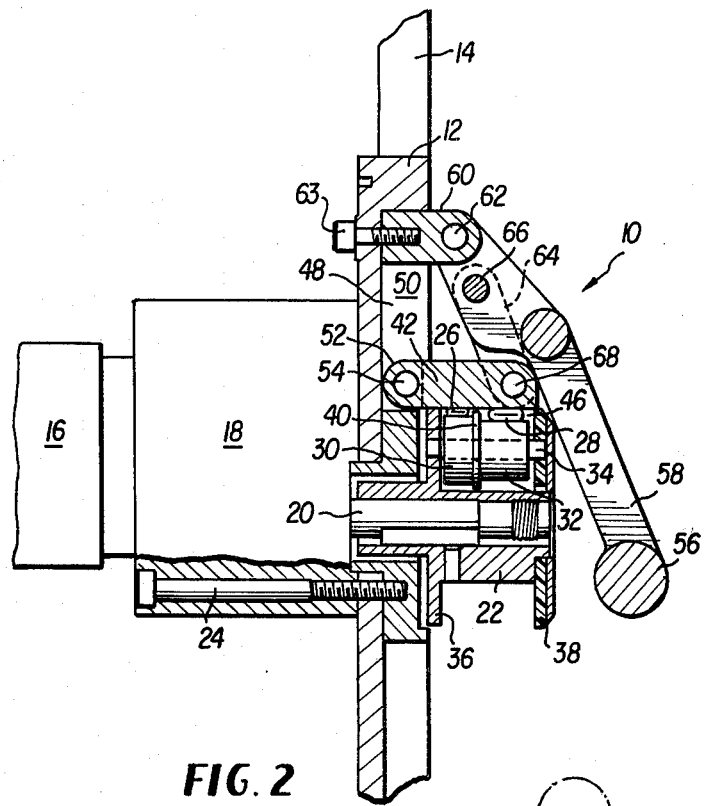
FIG. 2 is a partial, longitudinal cross-sectional view of the pump of FIG. 1 showing the pump pressure plate and operating handle actuating system when the pressure plate is disposed in its closed position.
Figure 3:
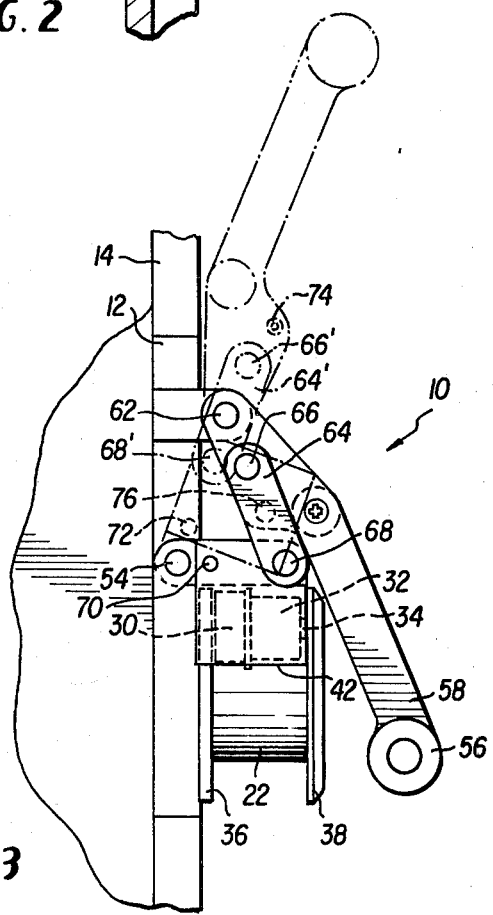
FIG. 3 is a side elevation view similar to that of FIG. 2 showing, in solid lines, the pump pressure plate and operating handle actuating system when the pressure plate is disposed in its closed position, and showing, in phantom lines, the pump pressure plate and operating handle actuating system when the pressure plate is disposed in its open position.

Referring now to the drawings, and more particularly to FIGS. 1-3 thereof, the peristaltic pump of the present invention is shown and generally indicated by the reference character 10. The pump includes a base member 12 mounted in a substantially recessed manner within a wall panel 14, and the operative components of the pump are in turn secured to the pump base 12. More particularly, the pump further comprises a drive motor 16 which is operatively connected with suitable reduction gearing housed within a reduction gear box 18. The reduction gearing 18 includes an axially extending drive shaft 20 which is keyed with a pump roller cage 22 so as to drivingly rotate the cage for performance of the pumping operations. The roller cage assembly 22, base member 12, and reduction gear box 18 are fixedly secured together by means of a plurality of bolts 24, only one of which is actually shown, for example, in FIG. 2.

The roller cage 22 houses three roller mechanisms equiangularly disposed thereabout at 120° intervals, only one of the roller mechanisms being shown in FIGS. 1 and 2. Depending upon whether or not the pump 10 is being utilized in conjunction with a single or multi-tube pumping system, the roller mechanisms may each comprise a single roller element upon which will be seated the single pump tube, or alternatively, a single stepped roller element or two co-axially mounted roller elements upon which will be seated the two tubes of the dual-tube pumping system. In FIGS. 1 and 2, there is exemplified a dual-tube pumping system comprising pump tubes 26 and 28 seated upon two co-axially disposed roller elements 30 and 32, respectively. The roller elements 30 and 32 are co-axially mounted upon a shaft 34, one end of which is disposed within an annular flanged portion 36 defined at the rear end of roller cage 22, while the opposite end of shaft 34 is disposed within a disk type cover 38 which serves to close the forward end of the roller cage assembly. Suitable bearing members, not shown, are interposed between the roller elements 30, 32 and the shaft 34 so as to permit the rollers to freely rotate upon shaft 34 as the roller cage 22 is rotated by means of the motor drive system. It is also seen that roller 30 is provided with an annular flange 40 defined at the forward end thereof. In this manner, it will be appreciated that tube 26 is able to be properly seated upon roller 30 due to the fact that the tube will be axially confined between roller cage flange 36 and roller element flange 40. In a similar manner, tube 28 is able to be properly seated and maintained upon roller 32 due to the fact that the tube will be axially confined between roller flange 40 and roller cage cover 38.

With reference still being made to FIGS. 1-3, in accordance with the present invention, the peristaltic pump 10 further comprises a roller guide element or pressure plate 42, and as best seen in FIG. 1, plate 42 is provided with a semi-cylindrical inner race 44 which operatively cooperates with the roller elements 30 and 32 so as to define a pumping chamber 46. In order to provide the desired and requisite accessibility to the pump chamber 46 so as to facilitate the pump tube loading and unloading procedures, pressure plate 42 is pivotably mounted upon pump base 12. In this manner, when the pump tubes 26 and 28 are to be inserted or removed from the pumping chamber 46, the pressure plate 42 may be moved away from its closed position, wherein the plate operatively cooperates with rollers 30 and 32 as shown in FIG. 2, to its open position as shown in FIG. 1 as well as in phantom lines in FIG. 3.

Pump base 12 includes a recessed compartment 48 defined within the upper portion thereof, compartment 48 being partially defined by means of sidewalls 50. Pressure plate 42 includes a pair of lugs 52 which extend rearwardly from the opposite sides thereof as viewed in FIG. 2, and the lugs are journalled within the base sidewalls 50 by means of pivot pins 54. In order to move pressure plate 42 between its open and closed positions, an operating handle 56 is operatively connected therewith. The handle includes a pair of parallel arms 58 the proximal ends of which are pivotably journalled within a support bracket 60 by means of pins 62. As best seen in FIG. 2, bracket 60 is fixedly secured within the uppermost region of compartment 48 by means of a plurality of bolts 63, only one of which is shown. A pair of links 64 complete the operative interconnection defined between the handle 56 and pressure plate 42, the links being pivotably secured to the exterior sidewalls of handle arms 58 and pressure plate 42 by means of a pintle shaft 66 and trunnions 68, respectively.

As may best be appreciated from FIGS. 1-3, and particularly FIG. 3 as such FIGURE discloses the relative positions of the various components when the pressure plate 42 is disposed in both its open and closed positions, the disposition of the pivotal axes of pressure plate 42 and handle 56, as defined by means of pivot pins 54 and 62, respectively, remains the same, relative to the entire mounting assembly, regardless of the movement of the pressure plate and handle. However, the disposition of the trunnions 68 and pintle shaft 66 varies depending upon the movement of the pressure plate 42 and handle 56. In effect, the various pivotal axes have determined a four-bar linkage system as defined between pivot points 54 and 62, 62 and 66, 66 and 68, and 68 and 54, respectively. This linkage arrangement is a mechanically-advantaged lever system for converting the operative movement of the handle 56 into a corresponding, although different, movement of pressure plate 42. In particular, due to the mechanical advantage defined by means of the aforenoted lever system, it is seen from FIG. 3, for example, that when the operating handle 56 undergoes movement from its lowered position to its raised position, it traverses an arcuate extent of approximately 140°. However, corresponding to such movement, the pressure plate traverses an arcuate extent of only approximately 65° between its closed and opened positions. The mechanically-advantaged system thus provides a simplified means for rapidly and efficiently moving the pressure plate between its open and closed positions so as to in effect simplify and expedite the pump tube loading and unloading procedures.

It is to be further appreciated that in accordance with the aforenoted linkage system, means are also defined for automatically retaining the handle 56 and the pressure plate 42 in either one of the raised and open, or lowered and closed, positions, respectively. More specifically, with particular reference still being made to FIG. 3, when the handle 56 is disposed in its extreme lowered position which corresponds to the pressure plate 42 being disposed in its closed, operative position, it is noted that the pivotal axes of the handle and the links, as defined by means of pivot pins 62, pintle shaft 66, and trunnions 68, are all substantially in a single plane, and in particular, the axis of pintle shaft 66 becomes substantially co-planarly aligned within the plane defined by means of the pivot points 62 and 68 when the pivot points move from their open positions 66' and 68' to their closed positions 66 and 68. In actuality, the shaft axis 66 moves a discrete distance beyond the plane defined by pivot points 62 and 68 whereby, in effect, an over-center type locking system is defined such that the handle and pressure plate are simply and securely retained in the closed position.

In a similar fashion, when the handle 56 is disposed in its extreme raised position which corresponds to the pressure plate 42 being disposed in its opened, inoperative position for facilitating the loading and unloading procedures for the pump tubes, the pivotal axes of the handle and the links, as defined by means of pivot pins 62, pintle shaft 66, and trunnions 68, are likewise all substantially disposed within a single plane, and furthermore, the axis of pintle shaft 66 again becomes substantially co-planarly aligned within the plane determined by means of the pivot points 62 and 68 when the pivot points move from their closed positions 66 and 68 to their opened positions 66' and 68'. Again, in actuality, the shaft axis 66 moves a discrete distance beyond the plane defined by pivot points 62 and 68 whereby, in effect, an over-center type locking system is again defined such that the handle and pressure plate are simply and securely retained in the opened position.

In order to further insure the retention of the handle and pressure plate in either one of the extreme opened or closed positions, and to audibly indicate to the operator the fact that the handle and pressure plate components have attained one of the extreme positions, detent means may be provided. Such means may take the form of a simple, spring-biased button or ball which operatively cooperates with a mating cavity. With respect to retaining the handle and pressure plate assembly in the opened position, the detent button may be provided upon each of the exterior sidewalls of the pressure plate as indicated by the reference character 70, the cooperating cavities 72 being provided upon the interior sidewalls 50 of the pump base 12. In a similar manner, with respect to retaining the handle and pressure plate in the closed position, detent buttons 74 are provided upon the exterior sides of each handle arm 58 while the detent cavities 76 are provided upon the interior sides of each link 64. As each of the detent buttons 70 and 74 mates with its respective cavity 72 and 76, an audible click indicates to the operator the fact that the handle and pressure plate components have attained one of the extreme positions.

As has been alluded to hereinbefore, while the pump of the present invention is applicable to single-tube and dual-tube pumping systems, the dual-tube system has in fact been illustrated. The dual-tube system is particularly useful in connection with human blood cell separator apparatus due to the fact that in accordance with current separator techniques, while the whole blood of the patient is being pumped by means of the pump apparatus through pump tube 28, an anti-coagulant fluid must be simultaneously pumped by means of the pump apparatus in order to prevent clotting of the patient's blood during the cell separating procedure. The anti-coagulant fluid is pumped through the narrow pump tube 26 and is combined with the whole blood from tube 28 at a position downstream of the pump apparatus 10.

In accordance with current cell separator techniques, a predetermined amount of anti-coagulant must be combined with the whole blood, and this relative amount varies from patient to patient. The pump apparatus of the present invention therefore includes means for accurately adjusting the relative amount or ratio of the anti-coagulant with respect to the whole blood volume being processed. This adjustment is accomplished by varying the volume flow rate of the anti-coagulant fluid through the pump tube 26.

Figure 4:
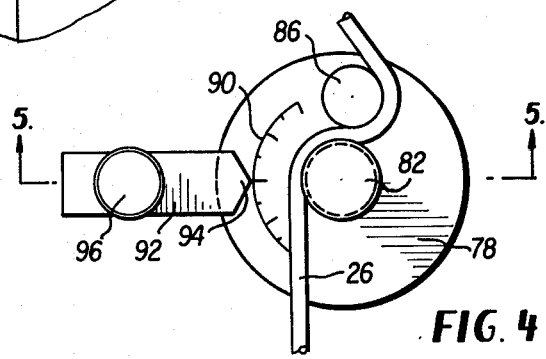
FIG. 4 is a front elevation view of the volume flow rate adjustment means utilized within the pump of FIG. 1.
Figure 5:
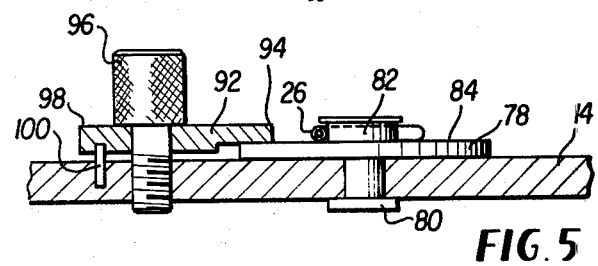
FIG. 5 is a cross-sectional view, taken along the line 5—5 of FIG. 4, of the volume flow rate adjustment means of FIG. 4.

With particular reference being made to FIGS. 1, 4, and 5, the anti-coagulant volume flow rate adjustment means is seen to comprise an adjustment plate 78 rotatably mounted upon the pump wall panel 14, at a position immediately below the pump roller cage assembly, by means of an axial rivet-type fastener 80. As best seen in FIG. 5, the fastener 80 has a stepped configuration with a large diameter flanged portion 82 projecting forwardly from the front surface 84 of plate 78. The flanged portion or guide 82, together with plate surface 84, thus serves to define an annular groove within a portion of which is disposed the small diameter pump tube 26.

A cylindrical tube guide 86 is fixedly secured to plate surface 84 at a radially spaced location relative to fastener portion 82, and a portion of pump tube 26 is trained about guide 86 so as to pass between the guides 86 and 82. The guides 86 and 82 thus serve to define a sinusoidal path for tube 26, the length of the sinusoidal path being variable depending upon the angular disposition of guide 86 relative to guide 82. For example, if the guide 86 were located at a position directly to the left of guide 82 such that the axes of the guides 86 and 82 defined a horizontal plane as viewed in FIGS. 1 and 5, then it would be appreciated that the length of the aforenoted sinusoidal path would in effect be zero due to the fact that the portion of tube 26 passing between the guides 86 and 82 would extend substantially vertically. However, as the adjustment plate 78 is rotated in a clockwise direction to the position illustrated, for example, the guide 86 is likewise moved in the clockwise direction whereby the length of the sinusoidal path is increased with a corresponding increase in the effective length of tube 26. As the ends 88 of the tube 26 are fixed to their nipple fittings in a conventional manner whereby the length of tube 26 trained about the roller cage assembly is fixed, an increase in the effective length of the tube 26 can only occur as a result of the tube being stretched. As a result of this stretching action, the diameter of the tube is concomitantly constricted whereby the volume flow rate of the anti-coagulant fluid flowing therethrough is altered. While the stretched and constricted properties of tube 26 will initially be somewhat confined to the vicinity of the aforenoted adjustment means, it has been experienced that with subsequent usage of the pump wherein the roller cage assembly rotates in the counterclockwise direction as indicated by the arrow A in FIG. 1, the tube 26 becomes uniformly stretched and constricted throughout its entire length within the pump apparatus.

In order to accurately predetermine the particular volume flow rate of the anti-coagulant fluid flowing through tube 26 relative to the volume flow rate of the whole blood flowing through tube 28, the adjustment plate 78 is provided with suitable indicia 90 which may be denoted in terms of volume flow rate percentages or ratios. Means are of course provided for retaining the adjustment plate 78 in a selected angular position in accordance with a relative predetermined required volume flow rate. Such means includes a locking finger 92, one end 94 of which overlaps the adjustment plate 78 so as to rest thereon. End 94 is also seen to be pointed and disposed adjacent the indicia 90 so as to accurately indicate the predetermined volume flow rate ratio selected. The locking finger 90 is mounted within wall panel 14 by means of a knurled locking bolt 96, and in order to prevent rotation of finger 92 about the axis of bolt 96, the end 98 of finger 92 opposite end 94 is fixed relative to panel 14 by means of a retaining pin 100. As can readily be appreciated, threaded adjustment of bolt 96 within panel 14 causes finger 92 to frictionally engage adjustment plate surface 84 whereby the latter is prevented from undergoing any angular movement. As a result, a predetermined volume flow rate within tube 26, relative to the volume flow rate occurring within large diameter tube 28, will be achieved and maintained.

Obviously, many modifications and variations of the present invention are possible in light of the foregoing teachings. It is therefore to be understood that within the scope of the appended claims, the present invention may be practiced otherwise than as specifically described herein.

What is claimed as new and desired to be secured by Letters Patent of the United States is:

1. A peristaltic pump comprising:
    a pump base;
    at least one pump tube through which a fluid is to be pumped;
    pump roller means rotatably mounted upon said pump base and operatively engaged with said at least one pump tube for pumping said fluid through said at least one pump tube;
    pressure plate means for defining a pumping chamber with said pump roller means, said pressure plate means being pivotably mounted upon said pump base for movement between a closed position whereby said pressure plate means operatively cooperates with said pump roller means for pumping said fluid through said at least one pump tube, and an open position whereby said pressure plate means is operatively disengaged from said pump roller means so as to render said pumping chamber accessible and thereby facilitate the loading and unloading of said at least one pump tube into and out of said pumping chamber;
    handle means permanently mounted in a pivotable mode upon said pump base for actuating said pressure plate means to either one of said open or closed positions; and
    a four-bar linkage system interconnecting said handle means and said pressure plate means.

2. A peristaltic pump as set forth in claim 1, wherein said four-bar linkage system comprises:
    a pair of links pivotably connected to both said pressure plate means and said handle means; and
    the bars of said linkage system are effectively defined between the pivotal axes of said pressure plate means and said handle means, between the pivotal axis of said handle means and the pivotal axis defined at the interconnection of said links and said handle means, between the pivotal axes of said links, and between the pivotal axis of said pressure plate means and the pivotal axis defined at the interconnection of said links and said pressure plate means, respectively.

3. A peristaltic pump as set forth in claim 1, further comprising:
    two pump tubes through which separate fluids are to be pumped.

4. A peristaltic pump as set forth in claim 3, wherein:

said two pump tubes have different diametrical dimensions whereby said separate fluids will be pumped at different volume flow rates.

5. A peristaltic pump as set forth in claim 4, wherein: said pump roller means comprises at least one set of co-axially mounted roller elements, said roller elements being of different diametrical extents so as to properly accommodate said different pump tubes.

6. A peristaltic pump as set forth in claim 5, wherein: said pump roller means comprises three sets of said co-axially mounted roller elements equiangularly disposed about the rotatable axis of said pump roller means.

7. A peristaltic pump as set forth in claim 4, further comprising:
   means for adjusting the volume flow rate of one of said pump tubes.

8. A peristaltic pump as set forth in claim 7, wherein: said means for adjusting the volume flow rate of one of said pump tubes comprises means for stretching said one of said pump tubes whereby the diameter of said one of said pump tubes is constricted.

9. A peristaltic pump as set forth in claim 8, wherein said means for stretching said one of said pump tubes comprises:
   a plate rotatably disposed adjacent said pump roller means so as to be movable to preselected angular positions;
   first pump tube guide means co-axially mounted upon said plate; and
   second pump tube guide means fixedly mounted upon said plate at a location radially spaced from said first pump tube guide means for defining with said first pump tube guide means a path for said one of said pump tubes,
   said one of said pump tubes being trained about and passing between said first and second pump tube guide means so as to extend along said path in a sinusoidal manner,
   whereby when said plate is rotated to various angular positions, the effective length of said sinusoidal path is increased thereby stretching said one of said pump tubes and constricting the diameter thereof so as to alter the volume flow rate of said one of said pump tubes.

10. A peristaltic pump as set forth in claim 9, further comprising:
    indicia means disposed upon said plate for indicating a predetermined volume flow rate ratio of said fluid within said one of said pump tubes relative to the volume flow rate of said fluid within the other one of said pump tubes.

11. A peristaltic pump as set forth in claim 2, further comprising:
    means for audibly indicating when said pressure plate means has achieved either one of its open or closed positions.

12. A peristaltic pump as set forth in claim 11, wherein:
    said audible indicating means comprises detent means defined between said pressure plate means and said pump base for signalling the opened position of said pressure plate means, and detent means defined between said handle means and said links for signalling the closed position of said pressure plate means.

13. A peristaltic pump as set forth in claim 2, further comprising:
    means for retaining said pressure plate means in either one of its open or closed positions.

14. A peristaltic pump as set forth in claim 13, wherein:
    said retaining means comprises detent means defined between said pressure plate means and said pump base for retaining said pressure plate means in its open position, and detent means defined between said handle means and said links for retaining said pressure plate means in the closed position.

15. A peristaltic pump comprising:
    a pump base;
    at least one pump tube through which a fluid is to be pumped;
    pump roller means rotatably mounted upon said pump base and operatively engaged with said at least one pump tube for pumping said fluid through said at least one pump tube;
    pressure plate means for defining a pumping chamber with said pump roller means, said pressure plate means being pivotably mounted upon said pump base for movement between a closed position whereby said pressure plate means operatively cooperates with said pump roller means for pumping said fluid through said at least one pump tube, and an open position whereby said pressure plate means is operatively disengaged from said pump roller means so as to render said pumping chamber accessible and thereby facilitate the loading and unloading of said at least one pump tube into and out of said pumping chamber;
    handle means permanently mounted in a pivotable mode upon said pump base for actuating said pressure plate means to either one of said open or closed positions; and
    a mechanically-advantaged lever system interconnecting said handle means and said pressure plate means whereby as a result of the movement of said actuating handle means, said pressure plate means is rapidly and efficiently moved between its open and closed positions.

16. A peristaltic pump as set forth in claim 15, wherein said mechanically-advantaged lever system comprises:
    a pair of links pivotably connected to both said pressure plate means and said handle means.

17. A peristaltic pump as set forth in claim 15, wherein:
    said mechanically-advantaged lever system defines an arcuate movement of said handle means which is approximately twice the arcuate movement of said pressure plate means as said pressure plate means moves between said open and closed positions.

18. A peristaltic pump comprising:
    a pump base;
    at least one pump tube through which a fluid is to be pumped;
    pump roller means rotatably mounted upon said pump base and operatively engaged with said at least one pump tube for pumping said fluid through said at least one pump tube;
    pressure plate means for defining a pumping chamber with said pump roller means, said pressure plate means being pivotably mounted upon said pump base for movement between a closed position whereby said pressure plate means operatively cooperates with said pump roller means for pumping said fluid through said at least one pump tube, and an open position whereby said pressure plate means is operatively disengaged from said pump roller means so as to render said pumping chamber accessible and thereby facilitate the loading and unloading of said at least one pump tube into and out of said pumping chamber;

handle means permanently mounted in a pivotable mode upon said pump base for actuating said pressure plate means to either one of said open or closed positions; and an over-center type locking linkage system interconnecting said handle means and said pressure plate means whereby said pressure plate means will be automatically secured in either its open or closed position.

19. A peristaltic pump as set forth in claim 18, wherein said over-center type linkage system comprises:

a pair of links pivotably connected to both said pressure plate means and said handle means.

20. A peristaltic pump as set forth in claim 19, wherein:

the pivotal axis of said handle means and the pivotal axis defined at the interconnection of said links and said pressure plate means define a movable plane; and the pivotal axis defined at the interconnection of said links and said handle means is disposed outside of said plane during movement of said handle means and said pressure plate means between said open and closed positions, and is substantially aligned with and substantially disposed within said plane when said pressure plate means is disposed at either one of said open or closed positions so as to achieve said over-center type locking action.

21. A peristaltic pump as set forth in claim 19, further comprising:

means for retaining said pressure plate means in either one of its open or closed positions.

22. A peristaltic pump as set forth in claim 21, wherein:

said retaining means comprises detent means defined between said pressure plate means and said pump base for retaining said pressure plate means in its open position, and detent means defined between said handle means and said links for retaining said pressure plate means in the closed position.

23. A peristaltic pump as set forth in claim 19, further comprising:

means for audibly indicating when said pressure plate means has achieved either one of its open or closed positions.

24. A peristaltic pump as set forth in claim 23, wherein:

said audible indicating means comprises detent means defined between said pressure plate means and said pump base for signalling the opened position of said pressure plate means, and detent means defined between said handle means and said links for signalling the closed position of said pressure plate means.

25. A peristaltic pump as set forth in claim 1, further comprising:

means for adjusting the volume flow rate of said at least one pump tube.

26. A peristaltic pump as set forth in claim 25, wherein:

said means for adjusting the volume flow rate of said at least one pump tube comprises means for stretching said at least one pump tube whereby the diameter of said at least one pump tube is constricted.

27. A peristaltic pump as set forth in claim 26, wherein said means for stretching said at least one pump tube comprises:

a plate rotatably disposed adjacent said pump roller means so as to be movable to selected angular positions;

first pump tube guide means co-axially mounted upon said plate; and second pump tube guide means fixedly mounted upon said plate at a location radially spaced from said first pump tube guide means for defining with said first pump tube guide means a path for said at least one pump tube, said at least one pump tube being trained about and passing between said first and second pump tube guide means so as to extend along said path in a sinusoidal manner, whereby when said plate is rotated to various angular positions, the effective length of said sinusoidal path is increased thereby stretching said at least one pump tube and constricting the diameter thereof so as to alter the volume flow rate of said at least one pump tube.

28. A peristaltic pump as set forth in claim 27, further comprising:

two pump tubes through which separate fluids are to be pumped.

29. A peristaltic pump as set forth in claim 28, wherein:

said two pump tubes have different diametrical dimensions whereby said separate fluids will be pumped at different volume flow rates.

30. A peristaltic pump as set forth in claim 29, further comprising:

indicia means disposed upon said plate for indicating a predetermined volume flow rate ratio of said fluid within said at least one pump tube relative to the volume flow rate of said fluid within the other one of said pump tubes.

31. A peristaltic pump as set forth in claim 30, further comprising:

means for retaining said plate in a predetermined angular position so as to maintain a selected volume flow rate ratio of said fluids.

* * * * *